United States Patent
Kim et al.

(10) Patent No.: US 7,094,608 B2
(45) Date of Patent: Aug. 22, 2006

(54) METHOD FOR MEASURING LANTHANIDE CONTENT DISSOLVED IN URANIUM OXIDE

(75) Inventors: Keon-Sik Kim, Daejeon (KR); Jae-Ho Yang, Daejeon (KR); Kun-Woo Song, Daejeon (KR); Ki-Won Kang, Daejeon (KR); Youn-Ho Jung, Daejeon (KR)

(73) Assignees: Korea Atomic Energy Research Institute, Daejeon (KR); Korea Hydro & Nuclear Power Co., Ltd., Seoul (KR)

( * ) Notice: Subject to any disclaimer, the term of this patent is extended or adjusted under 35 U.S.C. 154(b) by 582 days.

(21) Appl. No.: 10/307,153

(22) Filed: Nov. 27, 2002

(65) Prior Publication Data

US 2003/0194044 A1   Oct. 16, 2003

(30) Foreign Application Priority Data

Apr. 11, 2002   (KR) ...................... 10-2002-0019785

(51) Int. Cl.
*G01N 33/20* (2006.01)
*G21C 3/00* (2006.01)

(52) U.S. Cl. ........................... 436/82; 436/73; 436/81; 436/155; 436/160; 436/182; 376/412

(58) Field of Classification Search ............ 436/81–82, 436/147, 155, 160, 182, 73; 376/412
See application file for complete search history.

(56) References Cited

U.S. PATENT DOCUMENTS

| 4,134,064 A | * | 1/1979 | Jacobs et al. ................ 324/201 |
| 4,564,498 A | * | 1/1986 | Grossman et al. .......... 376/245 |
| 4,902,467 A | * | 2/1990 | Schoenig et al. ........... 376/159 |
| 5,073,915 A | * | 12/1991 | Zhang et al. .................. 378/54 |

FOREIGN PATENT DOCUMENTS

| JP | 62-50692 | * | 3/1987 |
| JP | 2-062959 |   | 3/1990 |
| JP | 7-198574 | * | 8/1995 |
| JP | 2000-147186 | * | 5/2000 |

OTHER PUBLICATIONS

You G -S.et al, Journal of Nuclear Materials 2000, 277, 325-332, no month.*
Kim J.-G et al, Journal of Nuclear Materials 2001, 297, 327-331, no month.*

* cited by examiner

*Primary Examiner*—Arlen Soderquist
(74) *Attorney, Agent, or Firm*—Bachman & LaPointe, P.C.

(57) ABSTRACT

The present invention relates to a method for measuring the content of Lanthanides dissolved in uranium oxide, wherein the Lanthanides content in the nuclear fuel pellet is measured using the thermo gravimetric analysis which measures the weight variation caused by the oxidation and heat treatment of the nuclear fuel pellet. This method provides an advantage in that the Lanthanide content can be measured using relatively simple equipments such as an electric furnace and a balance.

4 Claims, 4 Drawing Sheets

METHOD FOR MEASURING LANTHANIDE CONTENT DISSOLVED IN URANIUM OXIDE

FIELD OF THE INVENTION

The present invention relates to a method for measuring lanthanides content dissolved in uranium oxide, more particularly, a method for measuring the lanthanides content of a (U,La)O$_2$ nuclear fuel pellet, wherein the lanthanides content of the nuclear fuel pellet is measured using the thermo gravimetric analysis which measures the weight variation caused by the oxidation and heat treatment of the nuclear fuel pellet.

DESCRIPTION OF THE PRIOR ART

Nuclear reactors which generate nuclear fission energy use UO$_2$ as a nuclear fuel material, and further, a mixture of UO$_2$ and materials with strong neutron absorption may be used as well in order to control neutron. Lanthanides (hereinafter referred to as "La") such as Gd(Gadolinium), Er(Erbium), Eu(Europium) and Sm(Samarium) may be used as materials having such strong neutron absorption. Recently, among these, Gd is the most commonly used. The nuclear fuels containing such lanthanides are named as burnable absorbing nuclear fuel.

The method for preparing the burnable absorbing nuclear fuel is similar to the method for preparing the uranium oxide nuclear fuel. For example, as for (U,Gd)O$_2$, UO$_2$ powder is mixed with Gd$_2$O$_3$ powder and grinded, the grinded powder is then pre-molded at a pressure of about 1 ton/cm$^2$ to form a slug, and the slug is crushed to prepare granules. The granule is mixed with a lubricant and compression-molded to prepare a cylinder type green pellet. The green pellet is heated in a hydrogen atmosphere to a temperature of 1700–1780° C. and held for 2–6 hours. Such heating and holding are commonly referred as sintering. The nuclear fuel pellet comprising (U,Gd)O$_2$, wherein Gd$_2$O$_3$ is dissolved in UO$_2$, is prepared by the sintering process.

The La content dissolved in the (U,La)O$_2$ nuclear fuel, a burnable absorbing nuclear fuel, should be measured precisely since it greatly affects the nuclear fission of the nuclear fuel. The prior method for measuring the La content of the (U,La)O$_2$ nuclear fuel is as follows; the relative contents of various chemical components in a sample are measured from the intensity distribution using the energy dispersive X-ray spectrometry, and then the quantitative contents are determined by calibrating then with the standard sample having known La contents. Further, the prior method also has a disadvantage that the measured value may vary depending on the location of the sample and expensive equipments should be used.

SUMMARY OF THE INVENTION

Accordingly, the present inventors studied a method for measuring the La content dissolved in a (U,La)O$_2$ nuclear fuel pellet, and completed the present invention by measuring the La content of a nuclear fuel pellet using the thermo gravimetric analysis wherein the weight variation accompanied when the nuclear fuel pellet is oxidized and heat treated based on the characteristics of (U,La)O$_2$ nuclear fuel pellet as mentioned above.

It is an object of the present invention to provide a method for measuring the La content dissolved in a (U,La)O$_2$ nuclear fuel pellet.

DETAILED DESCRIPTION OF THE INVENTION

Figure 1:
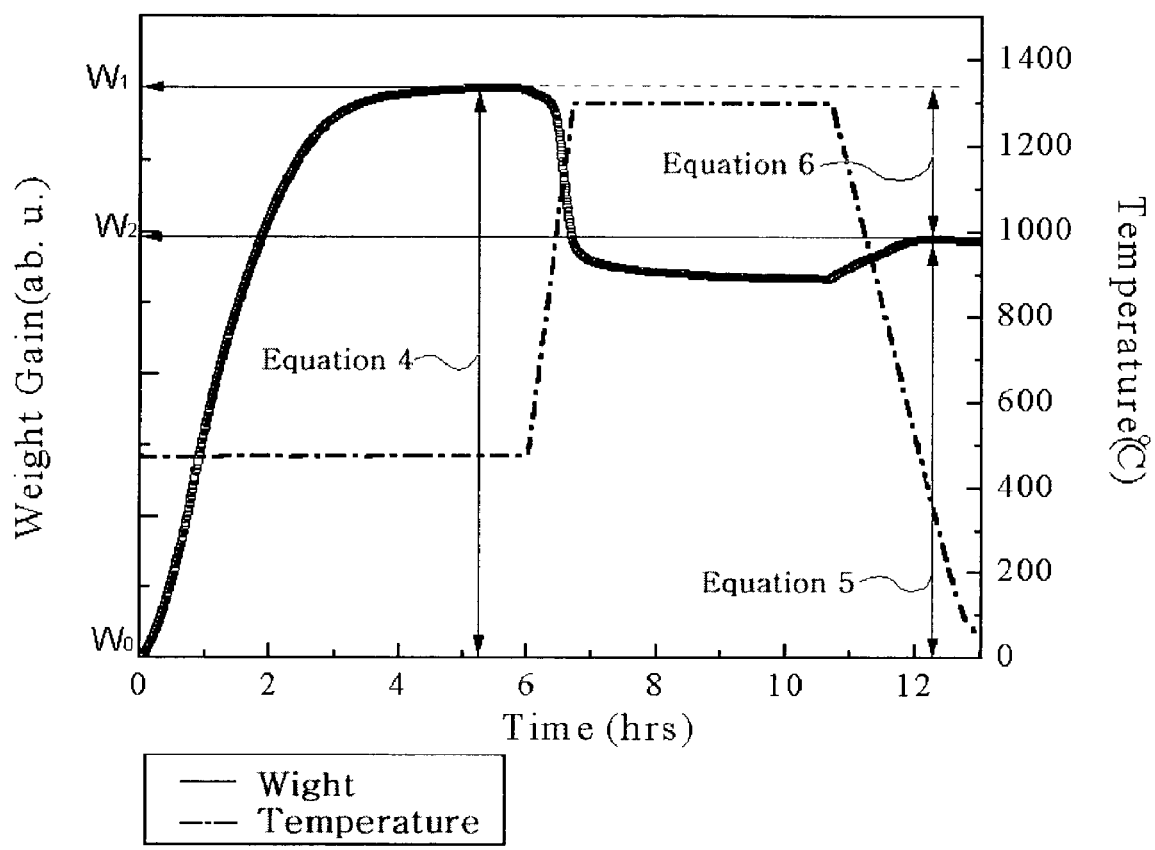
FIG. 1 is a graph showing the weight variation while the initial sample of the present invention is being heat treated.

Uranium oxide may exist as an oxide in the form of UO$_2$, U$_4$O$_9$ or U$_3$O$_8$ depending on the degree of oxidation of uranium, wherein UO$_2$ and U$_4$O$_9$ have a cubic lattice structure, and U$_3$O$_8$ has a orthorhombic lattice structure. The UO$_2$ pellet is oxidized to U$_3$O$_8$ at a temperature above 300° C. in a oxidizing atmosphere. Since the lattice volume of U$_3$O$_8$ is about 30% larger than that of UO$_2$, a lot of stress is generated while being oxidized, and accordingly, UO$_2$ pellet is spontaneously pulverized and then becomes U$_3$O$_8$ powder.

(U,La)O$_2$ nuclear fuel is a single phase having a structure wherein a part of the uranium ion is replaced with the La ion in the UO$_2$ lattice structure. Similar to the UO$_2$ pellet, the (U,La)O$_2$ pellet is oxidized to become (U,La)$_3$O$_8$ powder at a certain temperature above 300° C. in an oxidizing atmosphere. If the (U,La)$_3$O$_8$ powder is heat treated at a temperature above 950° C., La ion and U ion are diffused and (U,La)$_3$O$_8$ single phase is separated to two phase, U$_3$O$_8$ and (U,La)O$_{9/4}$. Whereas pure U$_3$O$_8$ does not display such phase separation even when it is heat treated. This is due to the fact that La ion is so unstable in (U,La)$_3$O$_8$ lattice structure that La ion diffuse out of (U,La)$_3$O$_8$ lattice and forms a new stable phase of (U,La)O$_{9/4}$ at high temperatures.

In order to attain the object, the present invention relates to a method for measuring the La content dissolved in a (U,La)O$_2$ nuclear fuel pellet. The said method consists of two combined procedures; One is to measure the weight variation caused by the oxidation of the (U,La)O$_2$ nuclear fuel pellet and the weight variation caused by the heat treatment of the oxidized pellet, and the other is to determine the content of La using the relations between the weight variations. More particularly, (U,La)$_3$O$_8$ powder is obtained when (U,La)O$_2$ nuclear fuel pellet is oxidized, and (U,La)O$_{9/4}$ phase and U$_3$O$_8$ phase are obtained when such (U,La)$_3$O$_8$ powder is additionally heat treated. That is, the La content can be measured by measuring the weight variation caused by the phase change when (U,La)O$_2$ nuclear fuel pellet is oxidized and heat treated.

The method can be elucidated in two cases wherein the O/(U+La) ratio of the (U,La)O$_2$ nuclear fuel pellet is known and unknown as the following.

First, when the O/(U+La) ratio of the (U,La)O$_2$ nuclear fuel pellet is not known the method for measuring the La content dissolved in (U,La)O$_2$ nuclear fuel pellet comprises steps of;

measuring the weight($W_1$) of $(U_{1-x}La_x)_3O_8$ powder obtained by oxidizing the $(U_{1-x}La_x)O_{2+Z}$ pellet in the oxidizing atmosphere at a temperature of 300–950° C. (step 1), measuring the total weight ($W_2$) of $(U_{1-y}La_y)O_{9/4}$ phase and $U_3O_8$ phase obtained by heat treating the $(U_{1-x}La_x)_3O_8$ powder in the inert or oxygen-containing atmosphere at a temperature of 950–1800° C. (step 2), and measuring the La content using the following equation 1 (step 3).

$$\frac{W_1 - W_2}{W_1} = \frac{MW_{O_2} \times \left(\frac{5x}{24y}\right)}{MW_{(U_{1-x}La_x)O_{8/3}}} \quad \text{(Equation 1)}$$

wherein, $MW_{O2}$ is the $O_2$ molecular weight, $MW_{(U1-xLax)O8/3}$ is the $(U_{1-x}La_x)O_{8/3}$ molecular weight, x is the La content dissolved in $(U,La)O_2$, and y is the La cation content dissolved in the $(U,La)O_{9/4}$ phase.

Preferably, step 1, which is a step measuring the weight ($W_1$) of $(U_{1-x}La_x)_3O_8$ powder obtained by oxidizing the $(U_{1-x}La_x)O_{2+Z}$ pellet, should be performed at the lowest temperature possible so that La ions are not diffused while being oxidized. The oxidation temperature is between 300° C. and 950° C., more preferably, between 400° C. and 800° C. In step 1, the U:La ratio of the $(U_{1-x}La_x)O_{2+Z}$ pellet is the same as that of the $(U_{1-x}La_x)_3O_8$ powder. In step 1, the oxidizing atmosphere should be an oxygen-containing gas.

In step 2, which is a step measuring the total weight ($W_2$) of $(U_{1-y}La_y)O_{9/4}$ phase and $U_3O_8$ phase separated by heat treating the $(U_{1-x}La_x)_3O_8$ powder, La ions and U ions are diffused to be so that the $(U_{1-y}La_y)O_{9/4}$ phase and $U_3O_8$ phase are separated. The higher the temperature, the faster the separation is completed. Preferably, the heat treatment temperature is 950–1800° C., more preferentially 1100–1500° C. Since $(U_{1-x}La_x)_3O_8$ is separated to $U_3O_8$ and $(U_{1-y}La_y)O_{9/4}$, the La content of the obtained $(U_{1-y}La_y)O_{9/4}$ phase is relatively higher than the La content of the $(U_{1-x}La_x)O_{2+Z}$ pellet. Even though the U:La ratio of the $(U_{1-x}La_x)O_{2+Z}$ pellet varies, the U:La rate of the $(U_{1-y}La_y)O_{9/4}$ powder is fixed in certain gas atmospheres. For example, the U:Gd ratio is 0.67:0.33 at 1300° C. in air.

In step 3, the La content is determined by the equation 1. Equation 1 can be derived as the following.

(1) The initial nuclear fuel is described in the following equation 3.

$$(U_{1-x}La_x)O_2 + \frac{z}{2}O_2 = (U_{1-x}La_x)O_{2+z} \quad \text{(Equation 3)}$$

wherein, x is the La content of $(U,La)O_2$, and z is the value when the O/(U+La) ratio of the initial sample is higher than 2.

(2) The oxidation reaction (step 1) wherein the $(U_{1-x}La_x)O_{2+z}$ phase is oxidized to $(U_{1-x}La_x)_3O_8$ phase is described in the following equation 4.

$$(U_{1-x}La_x)O_{2+z} + \frac{1}{3}O_2 - \frac{z}{2}O_2 = (U_{1-x}La_x)O_{8/3} \quad \text{(Equation 4)}$$

wherein, x and z are as described in equation 3.

(3) The reaction wherein the phase of the initial nuclear fuel pellet is separated to a equilibrium phase after being oxidized to $(U_{1-x}La_x)_3O_8$ is described in the following equation 5.

$$(U_{1-x}La_x)O_{2+z} + \frac{1}{3}O_2 - \frac{z}{2}O_2 - \frac{5x}{24y}O_2 = \quad \text{(Equation 5)}$$

$$\frac{x}{y}\left\{(U_{1-y}La_y)O_{\frac{9}{4}}\right\} + \left(1 - \frac{x}{y}\right)(UO_{8/3})$$

wherein, x and z are as described in equation 1 and equation 3.

(4) The reaction wherein $(U_{1-y}La_y)O_{9/4}$ phase and $U_3O_8$ phase are separated when the $(U_{1-x}La_x)_3O_8$ phase is heat treated to a high temperature is described in the following equation 6.

$$(U_{1-x}La_x)O_{8/3} - \frac{5x}{24y}O_2 = \quad \text{(Equation 6)}$$

$$\frac{x}{y}\left\{(U_{1-y}La_y)O_{\frac{9}{4}}\right\} + \left(1 - \frac{x}{y}\right)(UO_{8/3})$$

wherein, x and y are as described in equation 1.

FIG. 1 is a graph showing the weight variation while the initial sample of the present invention is being heat treated. The dotted line indicates the temperature change and the solid line indicates the weight change caused by the reactions described as equation 4–6.

(5) The $(W_1-W_2)/W_1$ can be derived from equation 6 as the following equation 1 wherein $W_1$ is the weight of the sample oxidized by equation 4 and $W_2$ is the weight of the sample that have been oxidized and phase separated by equation 6.

$$\frac{W_1 - W_2}{W_1} = \frac{MW_{O_2} \times \left(\frac{5x}{24y}\right)}{MW_{(U_{1-x}La_x)O_{8/3}}} \quad \text{(Equation 1)}$$

wherein, $MW_{O2}$ is the $O_2$ molecular weight, $MW_{(U1-xLax)O8/3}$ is the $(U_{1-x}La_x)O_{8/3}$ molecular weight, x is the La content dissolved in $(U,La)O_2$, and y is the La cation content dissolved in the $(U,La)O_{9/4}$.

When the La element is Gd, equation 1 can be described as the following equation 7.

$$\frac{W_1 - W_2}{W_1} = \frac{159.994 x'}{24y'(280.65 - 80.78 x')} \quad \text{(Equation 7)}$$

wherein, x' is the Gd content dissolved in (U,Gd)O$_2$, and y' is the Gd cation content dissolved in (U,Gd)O$_{9/4}$.

(W$_1$–W$_2$)/W$_1$ can be calculated from W$_1$ and W$_2$ measured from the experiment, and the La content x dissolved in the initial (U$_{1-x}$La$_x$)O$_{2+z}$ can be calculated from equation 1 by measuring the y' content in accordance with the present invention. In the meanwhile, when the La element is Gd, the y' content of the Gd cation dissolved in the (U$_{1-y}$Gd$_{y'}$)O$_{9/4}$ phase in proportion to the sample heat treated at 1300° C. is experimentally found to be 0.33. Since equation 1 is a function not related to the weight of the initial sample, information on the exact O/(U+La) ratio of the initial sample is not required.

Further, when the O/(U+La) ratio of the initial (U,La)O$_2$ nuclear fuel pellet is known, La content x can be calculated from (W$_0$–W$_2$)/W$_0$, in which is W$_0$ the initial weight (W$_0$) of the (U$_{1-x}$La$_x$)O$_{2+z}$ sample.

More particularly, a method for measuring the La content dissolved in (U,La)O$_2$ comprising steps of;

measuring the weight (W$_0$) of the (U$_{1-x}$La$_x$)O$_{2+z}$ pellet (step 1);

measuring the total weight (W$_2$) of the (U$_{1-y}$La$_y$)O$_{9/4}$ phase and U$_3$O$_8$ phase obtained by heat treating the (U$_{1-x}$La$_x$)$_3$O$_8$ powder obtained by oxidizing the (U$_{1-x}$La$_x$)O$_{2+z}$ pellet at 300–950° C. in the atmosphere at 950–1800° C. in the atmosphere (step 2);

measuring the La content using the following equation 2 (step 3).

$$\frac{W_0 - W_2}{W_0} = \frac{MW_{O_2} \times \left(\frac{5x}{24y} + \frac{z}{2} - \frac{1}{3}\right)}{MW_{(U_{1-x}La_x)O_{2+z}}} \quad \text{(Equation 2)}$$

wherein,

MW$_{O2}$ is the O$_2$ molecular weight,

MW$_{(U1-xLax)O2+z}$ is the (U$_{1-x}$La$_x$)O$_{2+z}$ molecular weight, x is the La content dissolved in (U,La)O$_{2+z}$, y is the La cation content dissolved in the (U,La)O$_{9/4}$ phase, and z is the value when the O/(U+La) ratio of the initial sample is higher than 2.

Equation 2 can be derivated as the following.

The ratio of the weight difference between the initial sample and the weight change after phase separation to the weight of the initial sample, that is, (W$_0$–W$_2$)/W$_0$ can be described as in the following equation 5.

$$\frac{W_0 - W_2}{W_0} = \frac{MW_{O_2} \times \left(\frac{5x}{24y} + \frac{z}{2} - \frac{1}{3}\right)}{MW_{(U_{1-x}La_x)O_{2+z}}} \quad \text{(Equation 2)}$$

The above equation can be described as equation 8 when the La element is Gd.

$$\frac{W_0 - W_2}{W_0} = \frac{15.9994(5x' + 12z'y' - 8y')}{12y'(270.03 - 80.78x' + 15.9994z')} \quad \text{(Equation 8)}$$

wherein, x' is Gd content dissolved in (U,Gd)O$_2$, y' is Gd cation content dissolved in the (U,Gd)O$_{9/4}$ phase, and z' is the value when the O/(U+Gd) ratio of the initial sample is higher than 2.

The (W$_0$–W$_2$)/W$_1$ can be calculated from W$_0$ and W$_2$ measured from the experiment when the O/(U+La) ratio of the initial sample is known, and the La content x of the initial sample can be calculated from equation 2 when the La cation content y dissolved in (U,La)O$_{9/4}$ phase and the O/(U+La) rate of the initial sample is known.

The lanthanides of the present invention include all lanthanides dissolved uranium oxide, preferably, they are selected from a group consisting of Gd(Gadolimium), Er(Erbium), (Eu)Europium and (Sm)Samarium, more preferably, they include Gd.

The present invention is described in more detail in the following example. This example is given only as an example to illustrate the content of the present invention and does not restrict the invention.

EXAMPLE 1

Measurement of Gd Content Dissolved in the (U,Gd)O$_2$ Nuclear Fuel Pellet

An (U,Gd)O$_2$ nuclear fuel pellet wherein 2 w % (2.951 mole %), 4 w % (5.846 mole %), 6 w % (8.685 mole %) and 10 w % (14.205 mole %) of Gd$_2$O$_3$ is dissolved in the UO$_2$ was prepared. Each nuclear fuel is respectively described as A, B, C, D, and the O/(U+Gd) ratio of each pellet is 2.00.

The initial weight (W$_0$) of the thus prepared nuclear fuel pellet sample A, B, C, D are 635.4 mg, 607.3 mg, 684.0 mg and 830.5 mg. Each sample has been oxidized at 475° C. in air for 4 hours and the weight of each sample were measured again. The weight of each oxidized sample A, B, C, D was 660.64 mg, 631.64 mg, 711.72 mg and 874.64 mg, respectively.

Each oxidized sample was heated in air at a rate of 600° C. per hour and was maintained at 1300° C. for four hours. Then each of them was cooled at a rate of 240° C. per hour and the weight of each sample (W$_2$) was measured at room temperature. The weight of each sample was 659.22 mg, 629.04 mg, 707.31 mg and 855.32 mg, respectively.

Figure 2:
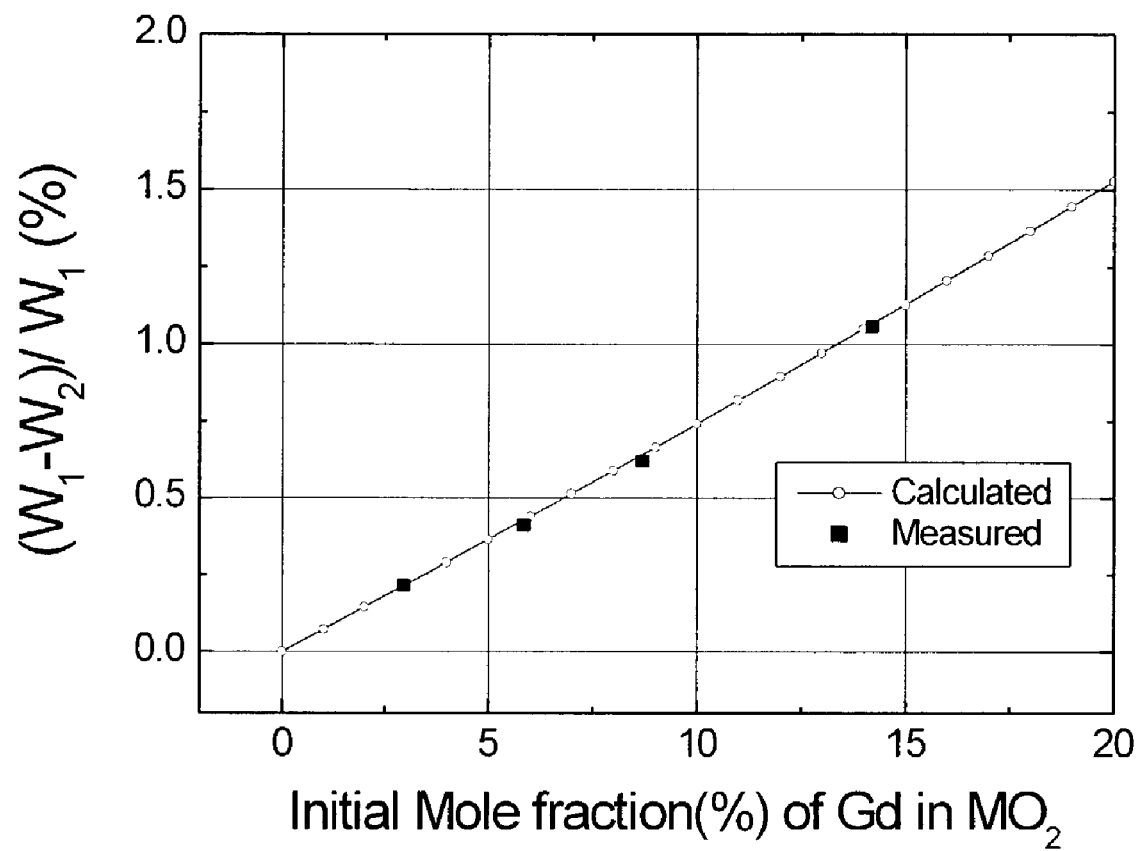
FIG. 2 is a graph comparing the calculated value and the measured value of the relation between the $(W_1-W_2)/W_1$ (%) value of the present invention and the initial mole fraction (%) of Gd in MO$_2$.
Figure 3:
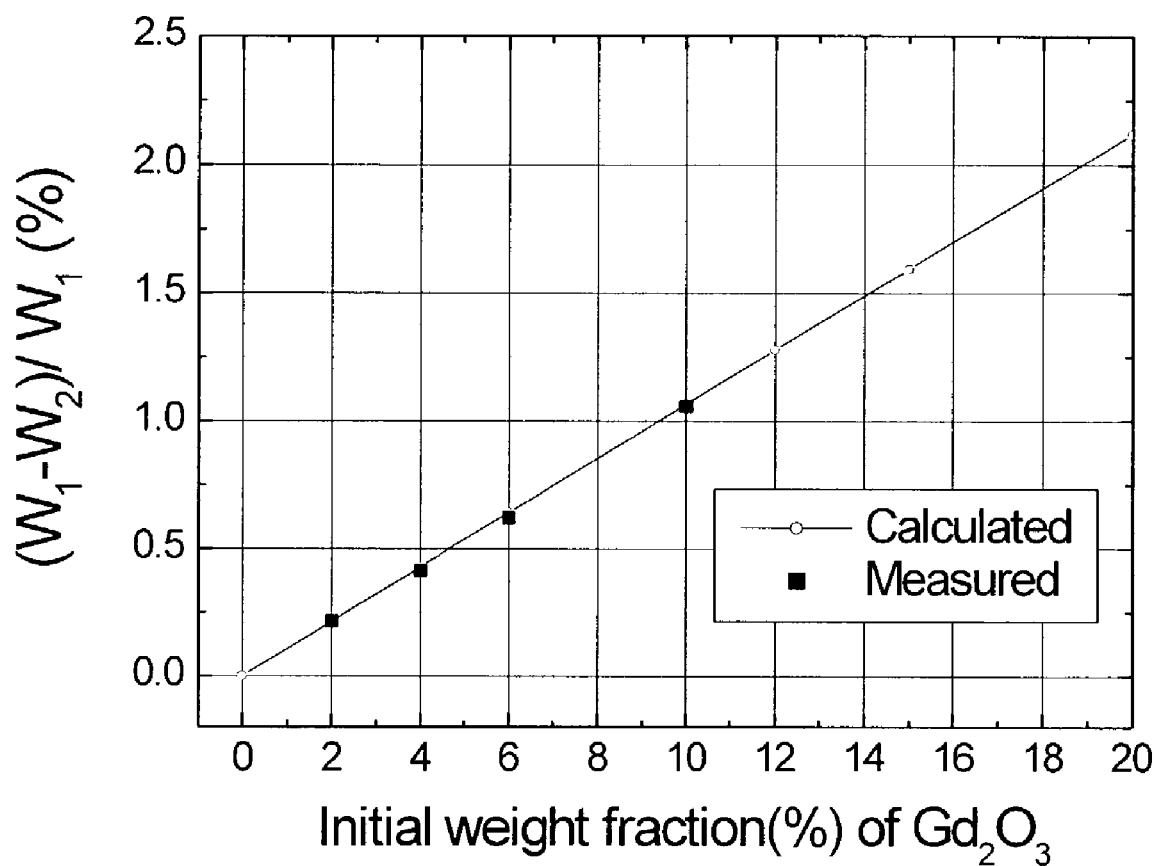
FIG. 3 is a graph comparing the calculated value and the measured value of the relation between the $(W_1-W_2)/W_1$ (%) value of the present invention and the initial mole fraction (%) of Gd$_2$O$_3$.
Figure 4:
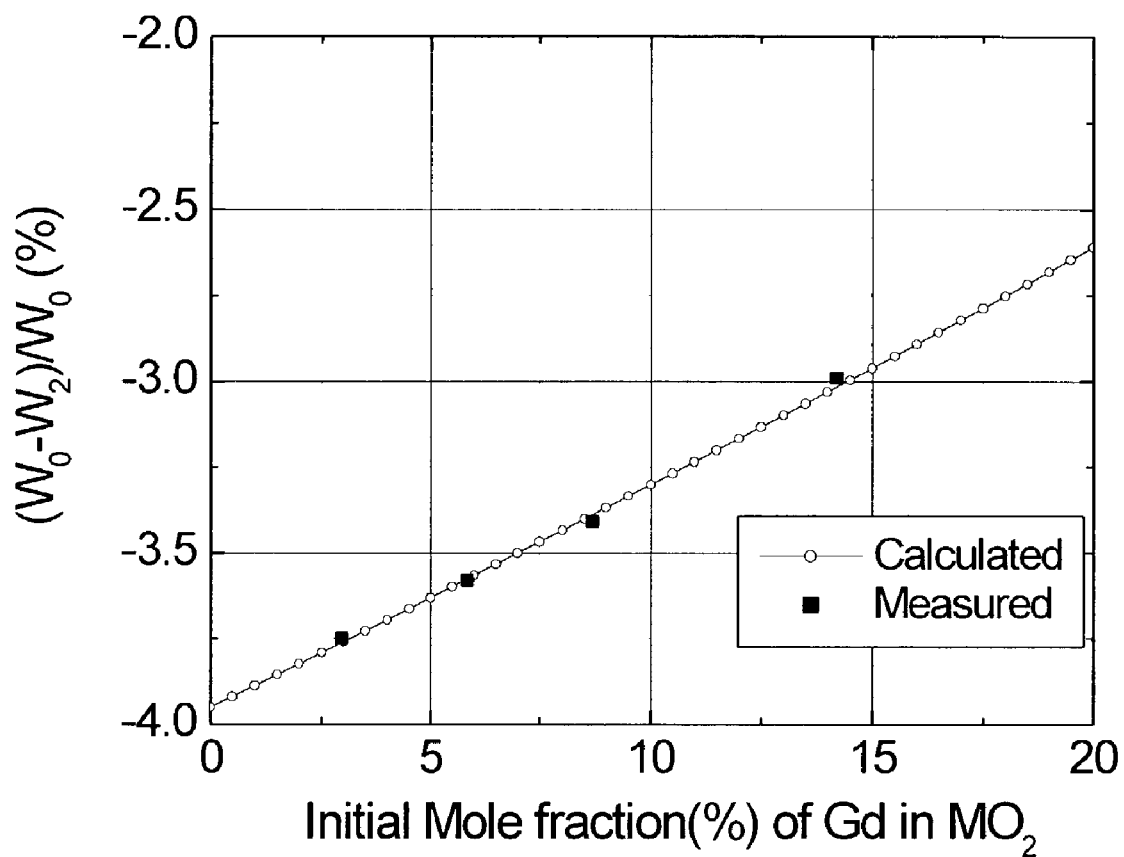
FIG. 4 is a graph comparing the calculated value and the measured value of the relation between the $(W_0-W_2)/W_0$ (%) value of the present invention and the initial mole fraction (%) of Gd in MO$_2$.

The W$_0$, W$_1$, W$_2$ value of sample A, B, C, D and the weight variation (W$_1$–W$_2$)/W$_1$ (%) and (W$_0$–W$_2$)/W$_0$ (%) calculated from these values are indicated in the following table 1. The values measured in accordance with the present invention are indicated in FIG. 2–FIG. 4.

TABLE 1

The W$_0$, W$_1$, W$_2$, (W$_1$–W$_2$)/W$_1$ (%) and (W$_0$–W$_2$)/W$_0$ (%) value of samples having various contents of Gd.

| Gd$_2$O$_3$ weight fraction in UO$_2$—Gd$_2$O$_3$ (%) | Gd mole fraction in (U,Gd) O$_2$ (%) | W$_0$ (mg) | W$_1$ (mg) | W$_2$ (mg) | (W$_1$–W$_2$)/ W$_1$ (%) | (W$_0$–W$_2$)/ W$_0$ (%) |
|---|---|---|---|---|---|---|
| 2 | 2.951 | 635.4 | 660.64 | 659.22 | 0.2149 | −3.749 |
| 4 | 5.846 | 607.3 | 631.64 | 629.04 | 0.4116 | −3.580 |

TABLE 1-continued

The $W_0$, $W_1$, $W_2$, $(W_1-W_2)/W_1$ (%) and $(W_0-W_2)/W_0$ (%) value of samples having various contents of Gd.

| $Gd_2O_3$ weight fraction in $UO_2$—$Gd_2O_3$ (%) | Gd mole fraction in $(U,Gd)\,O_2$ (%) | $W_0$ (mg) | $W_1$ (mg) | $W_2$ (mg) | $(W_1-W_2)/W_1$ (%) | $(W_0-W_2)/W_0$ (%) |
|---|---|---|---|---|---|---|
| 6 | 8.685 | 684.0 | 711.72 | 707.31 | 0.6196 | −3.408 |
| 10 | 14.205 | 830.5 | 964.46 | 855.32 | 1.0573 | −2.989 |

FIG. 2 is a graph comparing the calculated value obtained from equation 1 and the measured value (see table 1) obtained from the actual experiment; FIG. 3 is a graph wherein the value of FIG. 2 is converted to the $Gd_2O_3$ substituted at the nuclear fuel pellet; and FIG. 4 a graph comparing the calculated value obtained from equation 2 and the measured value (see table 1) obtained from the actual experiment. The Gd content of the $(U,Gd)O_{9/4}$ phase was determined experimentally to be 33 mole % from the EPMA analysis.

As shown in the above results, it is found out that the measured value and the calculated value of the Gd content in the $(U,Gd)O_2$ nuclear fuel of the present invention are exactly the same. Therefore, the $Gd_2O_3$ content of the $(U,Gd)O_2$ nuclear fuel pellet can be precisely measured using the method of the present invention.

EFFECT OF THE INVENTION

As described above, the method for measuring the La content of the $(U,La)O_2$ nuclear fuel pellet of the present invention is a method for measuring the La content dissolved in the nuclear fuel pellet by measuring the weight variation after the nuclear fuel pellet has been oxidized and heat treated. The La content dissolved in the $(U,La)O_2$ nuclear fuel pellet can be precisely measured more economically, since it can be measured using relatively simple equipments such as an electric furnace and a balance without using expensive precision instruments which were required using the prior measurements.

What is claimed is:

1. A method for measuring a La content dissolved in a $(U,La)O_2$ nuclear fuel pellet, wherein the method comprises a step of;
    measuring the weight $(W_1)$ of $(U_{1-x}La_x)_3O_8$ powder obtained by oxidizing a $(U_{1-x}La_x)O_{2+z}$ pellet in an oxidizing gas atmosphere at a temperature of 300–950° C. (step 1),
    measuring the total weight $(W_2)$ of $(U_{1-y}La_y)O_{9/4}$ phase and $U_3O_8$ phase obtained by heat treating the $(U_{1-x}La_x)_3O_8$ powder in an oxygen-containing gas or an inert gas atmosphere at a temperature of 950–1800° C. (step 2), and
    measuring the La content using the following equation 1(step 3)

$$\frac{W_1 - W_2}{W_1} = \frac{MW_{O_2} \times \left(\frac{5x}{24y}\right)}{MW_{(U_{1-x}La_x)O_{8/3}}} \quad \text{(Equation 1)}$$

wherein
    $MW_{O_2}$ is the $O_2$ molecular weight,
    $MW_{(U_{1-x}La_x)O_{8/3}}$ is the $(U_{1-x}La_x)O_{8/3}$ molecular weight,
    x is the La content dissolved in $(U,La)O_2$, and
    y is the La cation content dissolved in the $(U,La)O_{9/4}$ phase.

2. The method according to claim 1, wherein La is selected from a group consisting of Gd(Gadolinium), Er(Erbium), Eu(Europium) amd Sm(Samarium).

3. A method for measuring the La content dissolved in a $(U,La)O_2$ nuclear fuel pellet, wherein the method comprises steps of;
    measuring the weight($W_0$) of a $(U_{1-x}La_x)O_{2+z}$ nuclear fuel pellet(step 1),
    measuring the total weight $(W_2)$ of $(U_{1-y}La_y)O_{9/4}$ phase and $U_3O_8$ phase obtained by heat treating $(U_{1-x}La_x)_3O_8$ powder in an oxygen-containing gas pr am omert gas atmosphere at a tmeperature of 950–1800° C. (step 2), and
    measuring the La content using the following equation 2(step 3)

$$\frac{W_0 - W_2}{W_0} = \frac{MW_{O_2} \times \left(\frac{5x}{24y} + \frac{z}{2} - \frac{1}{3}\right)}{MW_{(U_{1-x}La_x)O_{2+z}}} \quad \text{(Equation 2)}$$

wherein,
    $MW_{O_2}$ is the $O_2$ molecular weight,
    $MW_{U_{1-x})O2+z}$ is the $(U_{1-x})_{Ohd\ 2+z}$ molecular weight,
    x is the La content dissolved in$(U,La)O_2$,
    y is the La cation content dissolved in the $(U,La)O_{9/4}$ phase, and
    z is the value when the O/(U+La) rate of the initial sample is higher than 2.

4. The method according to claim 3, wherein La is selected from a group consisting of Gd(Gadolinium), Er(Erbium), Eu(Europium) amd Sm(Samarium).

* * * * *

UNITED STATES PATENT AND TRADEMARK OFFICE
CERTIFICATE OF CORRECTION

PATENT NO. : 7,094,608 B2
APPLICATION NO. : 10/307153
DATED : August 22, 2006
INVENTOR(S) : Keon-Sik Kim et al.

Page 1 of 1

It is certified that error appears in the above-identified patent and that said Letters Patent is hereby corrected as shown below:

Col. 8 claim 2 line 3, "amd" should be corrected to read --and--.

Col. 8 claim 3 line 8, "pr am omert" should be corrected to read --or an inert--.

Col. 8 claim 3 line 9 "tmeperature" should be corrected to read --temperature--.

Col. 8 claim 3 line 9 after "1800°C" the following should be inserted --the($U_1$-xLax) 3O8 powder being obtained by oxidizing the ($U_1$-xLax)$O_2$+z nuclear fuel pellet in an oxidizing gas atmosphere at a temperature of 300-950°C--.

Col. 8 claim 3 line 15, "MWU1-x)02+z" should be corrected to read --MW($U_1$-xLax) $O_2$+z--.

Col. 8 claim 3 line 15, "(U1-x)Ohd 2+z" should be corrected to read --1-xLax)$O_2$+z--

Col. 8 claim 4 line 3, "amd" should be corrected to read --and--.

Signed and Sealed this

Fifth Day of December, 2006

JON W. DUDAS
*Director of the United States Patent and Trademark Office*

UNITED STATES PATENT AND TRADEMARK OFFICE
CERTIFICATE OF CORRECTION

PATENT NO. : 7,094,608 B2  Page 1 of 1
APPLICATION NO. : 10/307153
DATED : August 22, 2006
INVENTOR(S) : Keon-Sik Kim et al.

It is certified that error appears in the above-identified patent and that said Letters Patent is hereby corrected as shown below:

Col. 8 Claim 3 line 9, "(U1-xLax)3O8" should be corrected to read -- $(U_{1-x}La_x)_3O_8$ -- and "(U1-xLax)O2+z" should be corrected to read -- $(U_{1-x}La_x)O_{2+z}$ --.

Col. 8 Claim 3 line 15, "MWU1-x)02+z" should be corrected to read -- $MW_{(U1-xLax)O2+z}$ --.

Col. 8 Claim 3 line 15, "(U1-x)Ohd2+z" should be corrected to read -- $(U_{1-x}La_x)O_{2+z}$ --.

Signed and Sealed this

Third Day of April, 2007

JON W. DUDAS
*Director of the United States Patent and Trademark Office*